US010509004B2

(12) United States Patent
Harttig

(10) Patent No.: US 10,509,004 B2
(45) Date of Patent: Dec. 17, 2019

(54) SENSOR ELEMENTS WITH A TANTALUM- OR NIOBIUM-CONTAINING BASE LAYER AND METHODS OF PRODUCING THE SAME

(71) Applicant: Roche Diabetes Care, Inc., Indianapolis, IN (US)

(72) Inventor: Herbert Harttig, Neustadt (DE)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 95 days.

(21) Appl. No.: 15/195,064

(22) Filed: Jun. 28, 2016

(65) Prior Publication Data

US 2016/0305899 A1    Oct. 20, 2016

Related U.S. Application Data

(63) Continuation of application No. 14/059,983, filed on Oct. 22, 2013, now abandoned, which is a (Continued)

(30) Foreign Application Priority Data

Apr. 29, 2011    (EP) .................................. 11164256

(51) Int. Cl.
*G01N 27/327* (2006.01)
*G01N 27/30* (2006.01)
(Continued)

(52) U.S. Cl.
CPC ......... *G01N 27/307* (2013.01); *C23C 14/042* (2013.01); *C23C 14/165* (2013.01);
(Continued)

(58) Field of Classification Search
CPC ............ C23C 14/14–165; C23C 14/34; C23C 14/042–06; C23C 14/5873; G01N 27/307; G01N 27/327–3274
See application file for complete search history.

(56) References Cited

U.S. PATENT DOCUMENTS

| 2003/0106810 A1 | 6/2003 | Douglas et al. |
| 2004/0146899 A1* | 7/2004 | Kayyem ................ B82Y 15/00 |
| | | 435/6.11 |

(Continued)

FOREIGN PATENT DOCUMENTS

| WO | WO 2006/018447 A3 | 2/2006 |
| WO | WO 2008/002837 A3 | 1/2008 |

(Continued)

OTHER PUBLICATIONS

Advancement of Platinum Composite Electrode; Surface Technology, vol. 34, No. 5, pp. 16-18 (Chinese language, abstract attached).

*Primary Examiner* — Maris R Kessel
(74) *Attorney, Agent, or Firm* — Woodard, Emhardt, Henry, Reeves & Wagner, LLP

(57) ABSTRACT

Sensor elements are disclosed for the electrochemically analyzing a body fluid, as well as methods of producing and using the same. The sensor elements include an electrically conductive layer structure applied to a non-conductive carrier substrate, where the layer structure includes a continuous base layer of tantalum, niobium or an alloy thereof, and a metallic cover layer formed on the base layer that covers the base layer either over the entire surface or in some regions. The metallic cover layer includes a more noble metal when compared to the base layer.

21 Claims, 2 Drawing Sheets

Related U.S. Application Data continuation of application No. PCT/EP2012/057702, filed on Apr. 26, 2012.

(51) Int. Cl.
*C23C 14/04* (2006.01)
*C23C 14/16* (2006.01)
*C23C 14/34* (2006.01)
*C23C 14/58* (2006.01)

(52) U.S. Cl.
CPC .......... *C23C 14/34* (2013.01); *C23C 14/5873* (2013.01); *G01N 27/3272* (2013.01)

(56) References Cited

U.S. PATENT DOCUMENTS

| | | | |
|---|---|---|---|
| 2005/0019212 A1* | 1/2005 | Bhullar | G01N 27/3272 422/400 |
| 2005/0187097 A1* | 8/2005 | Huang | G01N 27/3272 502/101 |
| 2008/0003709 A1 | 1/2008 | Wegner | |
| 2009/0297913 A1 | 12/2009 | Zhang et al. | |
| 2010/0101965 A1 | 4/2010 | Sasaki et al. | |
| 2012/0186997 A1* | 7/2012 | Li | C12Q 1/00 205/778 |

FOREIGN PATENT DOCUMENTS

| WO | WO 2009/056299 A1 | 5/2009 |
|---|---|---|
| WO | WO 2009/144869 | 12/2009 |

* cited by examiner

SENSOR ELEMENTS WITH A TANTALUM- OR NIOBIUM-CONTAINING BASE LAYER AND METHODS OF PRODUCING THE SAME

CROSS-REFERENCE TO RELATED APPLICATIONS

This patent application is a continuation of U.S. application Ser. No. 14/059,983, filed Oct. 22, 2013, which is a continuation of Intl Patent Application No. PCT/EP2012/057702; filed 26 Apr. 2012, which claims the benefit of EP Patent Application No. 11164256.7; filed 29 Apr. 2011. Each patent application is incorporated herein by reference as if set forth in its entirety.

TECHNICAL FIELD

The disclosure relates generally to engineering and medicine, and more particularly to sensor elements for electrochemically analyzing a sample, as well as to production methods for such sensor elements.

BACKGROUND

Intl Patent Application Publication No. WO 2009/056299 discloses a generic biosensor with various structural regions in which the surface pattern of the layer structure is formed from different electrically conductive metals. For example, a first region made from a first electrically conductive material can be arranged on the substrate next to a second region made of a second electrically conductive material. The various regions can be connected together in an electrically conductive manner at connecting points of a few millimeters (mm) in width. Thus, the underside of the various metal layers of the layer structure are in planar contact with the substrate surface and must be specially structured on this surface. Varying transition resistances may result from the connecting points that only have a linear shape.

Additionally, Intl Patent Application Publication No. WO 2006/018447 discloses an electrochemical sensor system having a sandwich-like, 3D electrode structure. For example, a conductive layer can be formed by etching a continuous base layer made of gold (Au), silver (Ag), copper (Cu), aluminum (Al) or indium tin oxide (InSnO) and furnishing it with a metal coating made of platinum (Pt), Au or Ag in a region of an electrode surface that is to be formed. In this manner, it is intended to achieve improved electrochemical properties of the electrode surface.

On this basis, an object of this disclosure is to improve upon the known products and methods and to specify a reliable, simple-to-manufacture and material-saving construction for mass-producing biosensors.

BRIEF SUMMARY

The disclosure is based upon using multilayered, metallic combination layers for an electrically conductive layer structure.

In a first aspect, sensor elements are provided for electrochemically analyzing a sample, such as a body fluid sample, that include an electrically insulating carrier substrate and an electrically conductive layer structure deposited on the carrier substrate surface, where the layer structure has an electrode arrangement to which the sample can be applied.

In an embodiment, the electrically conductive layer structure can have a continuous metal base layer of tantalum (Ta), niobium (Nb) or an alloy thereof, and a metallic cover layer that is formed totally on the base layer and that covers the metal base layer either over the entire surface or in some regions thereof. The cover layer is at a distance from the carrier substrate surface. In another embodiment, the cover layer includes a noble metal.

The metals of the continuous metal base layer therefore can form the entire underside of the layer structure present on the substrate, which adheres to the carrier substrate surface. While the cover layer, as a whole, does not come into contact with the carrier substrate or has no contact with the carrier substrate surface, it can be used in a material-saving manner with a reduced layer thickness and where appropriate in areas of limited size such as, for example, only in functional areas. In this manner, the various base layer materials can be specifically adapted to their respective function by forming the continuous, strongly adherent, robust and electrically conductive base layer from a relatively inexpensive base metal and the electrochemically inert cover layer having durable surface properties from a noble metal. As such, the combination layers can be commonly structured in a composite.

Advantageously, the base layer can have a larger layer thickness than the cover layer such that the noble metal can be used in a manner that saves as much material as possible. In this manner, it is possible to restrict the cover layer to certain functional areas of the layer structure, where the cover layer covers about 5% or more of the total area of the base layer. Alternatively, the cover layer covers about 10% or more of the total area of the base layer.

To optimize the measuring success of particularly important functional areas, it is advantageous that the electrode arrangement and, where appropriate, a region of contact to the electrical connection of the electrode arrangement are formed from metals in two layers.

For electrochemical test elements, the cover layer can include a noble metal, such as Au. Alternatively, other noble metals such as palladium (Pd), Pt or an alloy thereof or therewith can be used as a material for the cover layer.

To reduce cost-intensive material usage, the cover layer can have a layer thickness of less than about 50 nm or alternatively less than about 20 nm.

In an embodiment, the base layer can be constructed entirely of Ta, which can be sputtered and forms a thin, dense, chemically passive oxide layer in air. The passive Ta oxide layer can prevent undesired additional signals due to electrochemically active surface behaviors from occurring in diagnostic sensors.

Surprisingly, it was found that Ta adheres substantially better than Au to the usual carrier substrates. The ductility of a sputtered Ta layer also remains relatively high, especially when gas impurities due to air and water in the sputter system are avoided. Moreover, Ta does not give rise to toxicological problems when used in diagnostic articles. In principle, all metals that also form a dense, chemically passive oxide layer in air can be used as a base layer. Examples include, but are not limited to, Nb, as well as alloys of Ta and Nb. However, for cost and processing reasons, Ta alone can be used.

The base layer can have an essentially constant layer thickness in the range of about 50 nm to about 200 nm. In an embodiment, a Ta base layer can be applied having a low layer thickness such as, for example, about 0.5 nm to about 10 nm onto a carrier substrate as an adhesive agent for an overlying bonding layer made of noble metal.

For specific tests, a reagent system can be designed for electrochemically detecting an analyte in the sample and can be arranged in a layered manner in a region of the electrode arrangement as described herein.

In a second aspect, methods are provided for producing the test sensors described herein that include a step of forming a layer structure from a continuous base layer made of Ta, Nb or an alloy thereof and, at least in some areas of a cover layer formed on the base layer that is made of a more noble metal when compared to the metal of the base layer.

Such a layer structure can be manufactured in a process suitable for mass production by firstly applying the base layer to the carrier substrate and subsequently applying the cover layer to the base layer by successive coating processes. In this manner, the base layer and the cover layer can be formed by sputter deposition. To obtain the highest possible quality of layer structure, the base layer and the cover layer can be successively sputtered on in a vacuum chamber without interrupting the vacuum.

To provide the functional areas, the cover layer can be applied to the base layer through a mask or aperture such as, for example, in a strip shape.

In an embodiment, the base layer and the cover layer can be geometrically structured together by removing material from sections by, for example, laser ablation.

In a third aspect, a method is providing for using test sensors as described herein as disposable electrochemical sensor elements in, for example, glucose tests. Alternatively, the test sensors can be configured for detecting other analytes such as, for example, lactate and coagulation parameters such as PT (prothrombin time).

These tests often are carried out repeatedly in an as cost-effective manner as possible, where high demands are made on the test accuracy and the body fluids to be examined result in special constraints. Moreover, the found resistance of the layer structure as described herein towards dissolution when stored in aqueous buffer proved its particular suitability for use in producing implantable or partially implantable sensors such as, for example, subcutaneous glucose sensors for the continuous measurement of glucose in subcutaneous adipose tissue.

These and other advantages, effects, features and objects of the invention will become better understood from the description that follows. In the description, reference is made to the accompanying drawings, which form a part hereof and in which there is shown by way of illustration, not limitation, embodiments of the invention.

BRIEF DESCRIPTION OF THE DRAWINGS

The advantages, effects, features and objects other than those set forth above will become more readily apparent when consideration is given to the detailed description below. Such detailed description makes reference to the following drawings, wherein.

Figure 1:
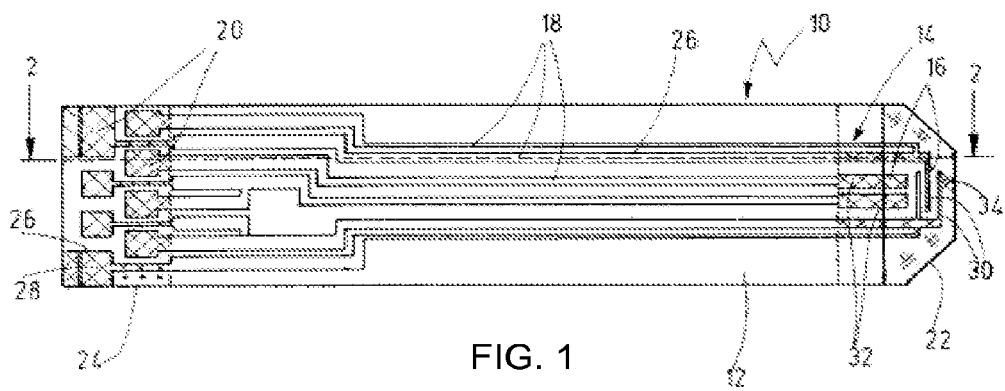
FIG. 1 shows an electrochemical sensor element having a two-layered metallic layer structure in certain areas in a top view.

While the present invention is susceptible to various modifications and alternative forms, exemplary embodiments thereof are shown by way of example in the drawings and are herein described in detail. It should be understood, however, that the description of exemplary embodiments that follows is not intended to limit the invention to the particular forms disclosed, but on the contrary, the intention is to cover all advantages, effects, features and objects falling within the spirit and scope of the invention as defined by the embodiments above and the claims below. Reference should therefore be made to the embodiments above and claims below for interpreting the scope of the invention. As such, it should be noted that the embodiments described herein may have advantages, effects, features and objects useful in solving other problems.

DESCRIPTION OF PREFERRED EMBODIMENTS

The sensor elements and methods now will be described more fully hereinafter with reference to the accompanying drawings, in which some, but not all embodiments of the invention are shown. Indeed, the inventions may be embodied in many different forms and should not be construed as limited to the embodiments set forth herein; rather, these embodiments are provided so that this disclosure will satisfy applicable legal requirements.

Likewise, many modifications and other embodiments of the sensor elements and methods described herein will come to mind to one of skill in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one."

Sensor Elements

Figure 2:
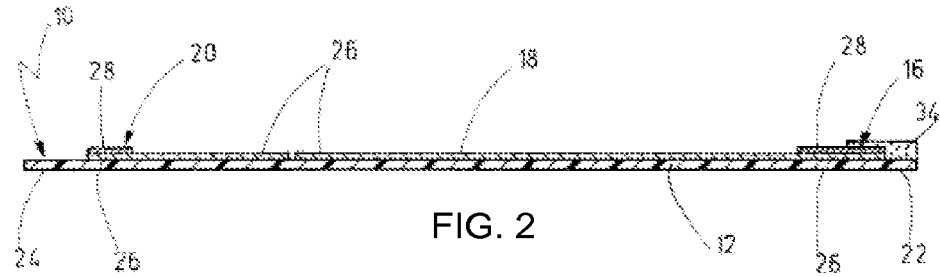
FIG. 2 shows the sensor element of FIG. 1 in a not-to-scale longitudinal section along the line 2-2.

The sensor element 10 shown schematically in FIGS. 1 and 2 can be used as a biosensor for electrochemically analyzing body fluids, and in particular in the form of a test strip for determining glucose in blood and/or tissue fluid. For this purpose, the sensor element 10 includes a non-conductive, strip-shaped carrier substrate 12 and applied thereto an electrically conducting layer structure 14 that has an electrode arrangement 16 to which the body fluid sample can be applied, electrical conductor paths 18 and contact pads 20 at the connecting end of the conductor paths 18. In the end sections 22, 24, which are bounded by dashed lines in FIG. 1, the layer structure 14 is formed from a thicker base layer 26 made of Ta as a base metal and a thinner cover layer 28 made of noble metal. In contrast, conductor paths 18 include a single layer only of the base layer 26 between the end sections 22, 24. The base layer 26 thus forms the entire base layer of the layer structure 14.

As further shown in FIG. 1, the electrode arrangement 16 has two measuring electrodes 30 and two control electrodes 32. A dry chemistry reagent system 34 can be applied in an area of at least one of the measuring electrodes 30 and can be swollen or dissolved by the body fluid sample to enable an analyte in the sample to be detected electrochemically by applying a voltage between the measuring electrodes 30.

FIG. 2 shows the electrode arrangement 16 in the end section 22 forming a measuring zone and the contact pads 20 in the end section 24 that can be connected to the instrument are together formed in two layers from the base and cover layer 26, 28 are connected by single layer conductor paths 18 in the base layer 26. The whole area of the underside of the base layer 26 can be in a permanently bonded contact with the substrate surface, while the cover layer 28 can be formed totally on the upper side of the base layer facing away from the carrier substrate and has no contact with the substrate surface.

The base layer 26, which is thicker relative to the cover layer 28, expediently consists of a highly electrically conductive metal when compared to the cover layer 28 such as a base metal and therefore is relatively inexpensive. Ta, Nb or alloys thereof are particularly suitable for this. A sufficiently robust base layer can have a layer thickness of, for example, about 50 nm.

As used herein, "about" means within a statistically meaningful range of a value or values such as a stated concentration, length, molecular weight, pH, sequence identity, time frame, temperature or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

The thinner cover layer 28 should be insensitive towards sample effects and offer a contact resistance that is as constant as possible and a constant electrochemical potential even over longer storage periods. Noble metals are particularly suitable for this, and can be, for example, Au; however, Pd, Pt or alloys made thereof or containing these coating substances also can be used. To minimize the cost of materials, the cover layer 28 should be as thin as possible and can have a layer thickness of less than about 50 nm or even less then about 20 nm.

The carrier substrate 12 can, as a cut-out, be made of a plastic foil material so that it can be simply processed in a mass production and is adequately stable for the intended use. The reagent system 34 can be formed from an enzyme composition and can be applied as a paste-like compound to the measuring zone 22, which subsequently can be dried to form a dry chemistry layer. Details of such electrochemical-enzymatic biosensors are known to one of skill in the art and do not need to be elucidated in more detail herein.

When used once as intended, a blood sample is applied by a user onto the electrode arrangement 16, and the test strip 10 then is evaluated in a hand-held instrument (not shown). The instrument applies an electrical potential to the electrode arrangement 16 via the contact pads 20 and registers a response (e.g., current, impedance, charge, etc.), which depends on the presence or concentration of an analyte such as, for example, blood glucose. After use, the test strip 10 is disposed of.

Methods of Making Sensor Elements

Figure 3:
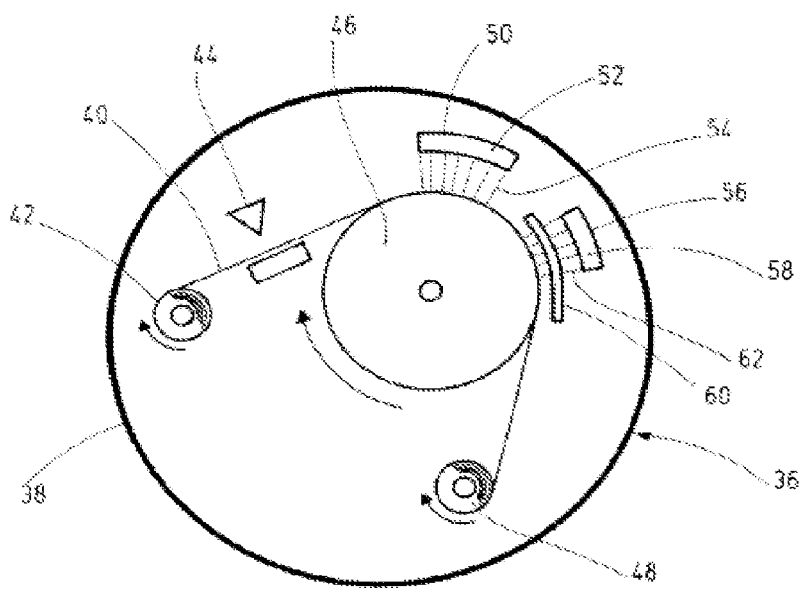
FIG. 3 shows an illustrative diagram of a sputter system for producing the layer structure.

FIG. 3 shows an exemplary method for mass producing substrates 12 having a metal layer structure 14 in a sputter system 36. A carrier foil tape 40 can be pulled from a supply roll 42 in a vacuum chamber 38 of the sputter system 36, pulled past a corona station 44 for surface treatment and deflected by a coating roller 46 onto a product roll 48 where it is wound on again.

The base layer 26 can be applied over the entire area at a first sputter station 50 in the region of the coating roller 46. For this purpose, the target material is removed from, for example, a Ta target 52 by ion bombardment and the sputtered particles 54 are condensed onto the foil surface to form the base layer 26. In the course of further tape transport, an Au target 58 can be atomized at a second sputter station 56 to build up the cover layer 28 above the base layer 26. A water-cooled aperture 60 can be used to delimit regions of the cover layer 28, through the openings of which the sputtered Au 62 is deposited on the base layer 26 only in strip-shaped areas. The optional noble metal can be deposited on the aperture 60 and can easily be reclaimed. To avoid forming interfering oxides on the base layer 26, the cover layer 28 can be immediately deposited on the base layer 26 after the base layer 26 has been deposited without interrupting the vacuum and with the exclusion of nitrogen, oxygen, hydrogen and water vapour (i.e., within seconds or fractions of seconds depending on the transport speed of the carrier foil 40).

The product roll 48 removed from the vacuum chamber 38 can be spooled through a laser station in a further process step to form a geometric surface pattern of the layer structure 14. In this manner, a laser light is beamed in a planar manner through a mask onto sections of the tape material 40, and as a result, the layer material is removed outside the desired layer structure 14. Such a laser ablation technique is known in the art and is described in, for example, Intl Patent Application Publication No. WO 2009/056299.

Laser ablation is effective and inexpensive and results in much less work than etching which is important especially for mass products. The laser pulse in ablation results in a metal vapor cloud that has to be sucked up as completely as possible. Nevertheless, it is unavoidable in practice that metal particles are deposited on the substrate and electrode areas. In this manner, it must be taken into consideration that the mask is arranged at a relatively large distance and does not allow a covering. With Au, this effect is harmless because Au electrodes are used anyway, whereas with other metals, the deposit usually is electrochemically active if they contain base elements such as, for example, Cu. Ta, however, remains surprisingly stable due to a dense metal oxide surface. In this connection, it should also be taken into consideration that laser ablation occurs in air in which oxygen is available. The surface of the ablation particle therefore always should be covered in oxide so that it has hardly any impact when deposited on the electrodes and results comparable to those of pure Au are achieved.

In a production step that follows the laser ablation, the tape material 40 can be provided with the reagent system 34 and cut into individual strips 10.

A layer structure 14 produced in this manner includes, for example, a base layer made of Ta of about 50 nm to about 70 nm thickness covered with a cover layer made of Au of about 10 nm thickness. A chemically passive, non-conducting Ta oxide layer forms in the region of the conducting paths 18 in which the bare Ta comes to lie due to the effect of atmospheric oxygen. The oxidation of Ta can be accelerated even more due to the short-term, very high temperature during laser ablation such that the oxide layer is formed in an adequate thickness to be chemically completely passive at the remaining edges and on the tantalum dust that is formed. Au dust formed during laser ablation is inert.

The layer thickness of the base layer 26 firstly depends on the desired electrical properties (i.e., adequate conductivity). On the other hand, it should not be too thick for the ablation so that a compromise has to be found. It also must be taken into consideration that the sensitivity to breakage increases with thicker layers. A further constraint is the cost of materials. Ta currently is still two orders of magnitude cheaper than Au, which causes a considerable cost factor in conventional disposable test elements. When Ta is used as the base layer, an imperfect, thin Au layer also can suffice as a cover layer. This is due to the fact that faults such as pores or so-called pin holes only expose the underlying Ta oxide layer, which is electrochemically substantially neutral. Although in comparison to sputtering it is possible to make more perfect layers by vaporization, for example, electron beam vaporization, the required vacuum process is, however, more complex.

Instead of Au, it also is possible to use Au—Pd alloys as a noble metal. This has the advantage that a closed layer is already formed with smaller thicknesses. Au—Pd alloys containing about 80/20% to about 60/40% are readily available.

If Pt is used as a cover layer on a Ta base layer, particularly thin layers of noble metal can be achieved. In the case of about 2.5 nm Pt on about 50 nm Ta, the cost of materials for the layer structure per test can be reduced by more than 90% when compared to pure Au with a thickness of about 50 nm. If Pd on Ta is used, one can profit from the cheaper price of Pd and the ability to manufacture relatively thin layers.

EXPERIMENTAL

The invention will be more fully understood upon consideration of the following non-limiting examples, which are offered for purposes of illustration, not limitation.

Example 1

In a comparative experiment, a pure Au layer and various Ta—Au layer structures were sputtered onto a carrier foil (Melinex® 329; DuPont Teijin Films) as described above and examined with regard to electrochemical properties and adhesiveness.

An overview of possible electrode processes was obtained from the generated patterns by cyclovoltammetry in an aqueous base electrolyte at 22° C. The base electrolyte was prepared from double distilled $H_2O$ (400 ml; $KH_2PO_4$ (2.07 g), $K_2HPO_4$ (4.86 g), NaCl 0.9% (3.6 g), Triton X100 (0.42 g)) having a pH of 7.0±0.1. The cyclovoltamogramms of FIGS. 4 and 5 were obtained by applying a saw tooth voltage. The current intensity (I) in relation to the potential (E) at the formed layer electrode was recorded for several cycles.

Figure 4:
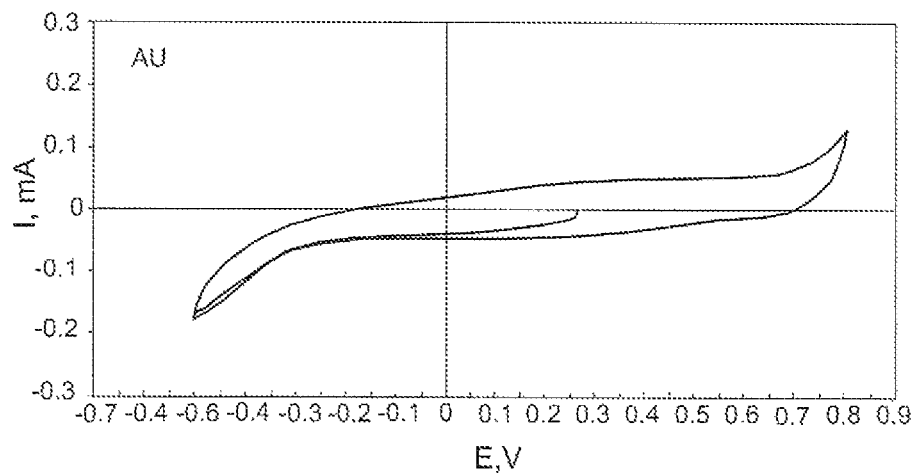
FIGS. 4 and 5 show cyclovoltamogramms of a comparative experiment.
Figure 5:
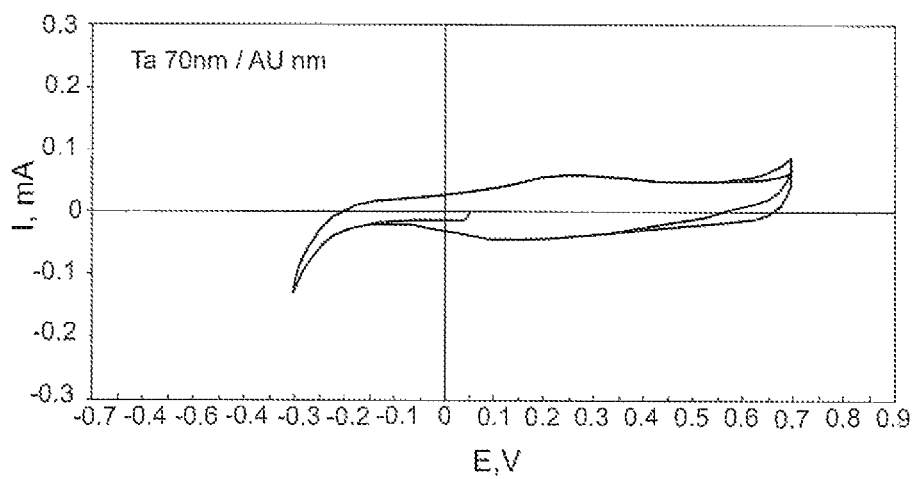

FIG. 4 shows that no substantial electrode reactions occur in a range from −0.5 to +0.8 V for pure Au, which would otherwise lead to a peak in the current-potential curve. Also no interfering electrode processes in the potential range of −0.3 to +0.7 V were found for a layer electrode made of a base layer of Ta (70 nm thickness) and a cover layer of Au (10 nm thickness). In this manner, it should be taken into account that measuring voltages for electrochemical sensor elements usually lie in this range at, for example, 0.35 V. It also should be noted that an Au layer of only 10 nm thickness does not form a perfect surface and that nevertheless such a Ta—Au electrode emits no interfering electroactive signals.

With regard to adhesion on the substrate, it was found that an Au layer of 50 nm thickness could be completely rubbed off with little effort by thumb pressure using an absorbent paper after 72 hours storage in buffer solution (base electrolyte according to the above-mentioned formulation) at room temperature. In contrast, a coating having of a base layer of 50 nm Ta and a cover layer of 30 nm Au could not be rubbed off under the same conditions any more than a coating of a base layer of 70 nm Ta and a cover layer of 10 nm Au. Hence, the adhesion of a Ta—Au combination layer on the Melinex® 329 substrate was surprisingly substantially better than that of pure Au.

The improved adhesion compared to Au also was observed with laser ablation. Whereas in the case of a coating of 50 nm Au, the edges of the layer remaining on the substrate lifted and warped up to several pm distance from the edge of the substrate, which was not observed for a coating consisting of a base layer of 50 nm Ta and a cover layer of 30 nm Au.

All of the patents, patent applications, patent application publications and other publications recited herein are hereby incorporated by reference as if set forth in their entirety.

The present invention has been described in connection with what are presently considered to be the most practical and preferred embodiments. However, the invention has been presented by way of illustration and is not intended to be limited to the disclosed embodiments. Accordingly, one of skill in the art will realize that the invention is intended to encompass all modifications and alternative arrangements within the spirit and scope of the invention as set forth in the appended claims.

The invention claimed is:

1. A sensor element for electrochemically analyzing a body fluid sample, the sensor, element comprising:
    an electrically insulating carrier substrate; and
    an electrically conductive layer structure deposited on a surface of the electrically insulating carrier substrate, wherein the electrically conductive layer structure comprises a continuous base layer of tantalum, niobium or an alloy thereof and a metallic cover layer formed only on the base layer covering the base layer only in some regions thereof, wherein the cover layer is a noble metal which is more noble than the base layer, and wherein the electrically conductive layer structure includes an electrode arrangement to which the body, fluid sample can be applied,
    the electrically conductive layer structure also including, contact pads for making electrical contact with an instrument for applying electrical potential to the sensor element, and conductive paths extending between the electrode arrangement and the contact pads, the electrode arrangement including portions of the base layer and the cover layer, the contact pads including portions of the base layer and the cover layer; and the conductive paths including portions of the base layer free of the cover layer.

2. The sensor element of claim 1, wherein the cover layer covers about 5% or mire of the total area of the base layer.

3. The sensor element of claim 1, wherein the base layer has a greater layer thickness than the cover layer.

4. The sensor element of claim 1, wherein the base layer has an essentially constant layer thickness in the range of about 50 nm to about 200 nm.

5. The sensor element of claim 1, wherein the cover layer has a layer thickness of less than about 50 nm.

6. The sensor element of claim 1, wherein the cover layer has a layer thickness of less than about 20 nm.

7. The sensor element of claim 1, wherein the base layer as an adhesive agent for the cover layer has a layer thickness of at least about 0.5 nm and less than about 20 nm.

8. The sensor element of claim 1, wherein the base layer is entirely tantalum.

9. The sensor element of claim 1, wherein the cover layer is a noble metal selected from the group consisting of gold, palladium, platinum and alloys thereof.

10. The sensor element of claim 9, wherein the noble metal is gold.

11. The sensor element of claim 1, wherein the electrode arrangement and a region of contact to an electrical connection of the electrode arrangement are formed from metals in two layers.

12. The sensor element of claim 1, further comprising a reagent system for electrochemically detecting an analyte in the sample, wherein the reagent system is arranged in a region of the electrode arrangement.

13. The sensor element of claim 12, wherein the reagent system is configured for glucose, lactate or prothrombin time testing.

14. A sensor element for electrochemically analyzing a body fluid sample, the sensor element comprising:
an electrically insulating carrier substrate comprised of a plastic foil material; and
an electrically conductive layer structure deposited on a surface of the carrier substrate, the electrically conductive layer structure including an electrode arrangement to the which the body fluid sample can be applied, contact pads for making electrical contact with an instrument for applying electrical potential to the sensor element, and a conductive paths extending between the electrode arrangement and the contact pads;
wherein the electrically conductive layer structure comprises a continuous base layer of tantalum, niobium or an alloy thereof and a metallic cover layer formed only on the base layer covering the base layer only in some regions thereof;
wherein the cover layer is a noble metal which is more noble than the base layer;
wherein the electrode arrangement includes portions of the base layer covered by the cover layer;
wherein the contact pads include portions of the base layer covered by the cover layer; and
wherein the conductive paths include portions of the base layer, not covered by the cover layer.

15. The sensor element of claim 14, wherein the base layer has a greater layer thickness than the cover layer.

16. The sensor element of claim 14, wherein the base layer has an essentially constant layer thickness in the range of about 50 nm to about 200 nm.

17. The sensor element of claim 14, wherein the cover layer has a layer thickness of less than about 50 nm.

18. The sensor element of claim 14, wherein the base layer is entirely tantalum.

19. The sensor element of claim 14, wherein the cover layer is a noble metal selected from the group consisting of gold, palladium, platinum and alloys thereof.

20. The sensor element of claim 19, wherein the noble metal, is gold.

21. The sensor element of claim 14, further comprising a reagent system for electrochemically detecting an analyte in the sample, wherein the reagent system is arranged in a region of the electrode arrangement.

* * * * *